(12) United States Patent
Eversull et al.

(10) Patent No.: US 7,765,014 B2
(45) Date of Patent: Jul. 27, 2010

(54) APPARATUS AND METHODS FOR DELIVERING TRANSVENOUS LEADS

(75) Inventors: Christian S. Eversull, Palo Alto, CA (US); Stephen A. Leeflang, Sunnyvale, CA (US); Nicholas J. Mourlas, Mountain View, CA (US)

(73) Assignee: Medtronic, Inc., Minneapolis, MN (US)

( * ) Notice: Subject to any disclaimer, the term of this patent is extended or adjusted under 35 U.S.C. 154(b) by 1015 days.

(21) Appl. No.: 11/465,113

(22) Filed: Aug. 16, 2006

(65) Prior Publication Data

US 2007/0043413 A1 Feb. 22, 2007

Related U.S. Application Data

(60) Provisional application No. 60/708,750, filed on Aug. 16, 2005.

(51) Int. Cl.
*A61N 1/00* (2006.01)
(52) U.S. Cl. ..................................... 607/122
(58) Field of Classification Search ................ 607/122, 607/127, 119; 600/585
See application file for complete search history.

(56) References Cited

U.S. PATENT DOCUMENTS

| | | | |
|---|---|---|---|
| 4,650,472 A | 3/1987 | Bates | |
| 4,774,949 A | 10/1988 | Fogarty | |
| 4,995,878 A | 2/1991 | Rai | |
| 5,267,958 A | 12/1993 | Buchbinder et al. | |
| 6,007,517 A | 12/1999 | Anderson | |
| 6,007,522 A | 12/1999 | Argo et al. | |
| 6,312,406 B1 | 11/2001 | Jayaraman | |
| 6,979,290 B2 | 12/2005 | Mourlas et al. | |
| 2004/0116878 A1* | 6/2004 | Byrd et al. | ................... 604/263 |
| 2005/0149104 A1 | 7/2005 | Leeflang et al. | |
| 2005/0149105 A1 | 7/2005 | Leeflang et al. | |
| 2006/0217755 A1 | 9/2006 | Eversull et al. | |
| 2007/0083187 A1 | 4/2007 | Eversull et al. | |

* cited by examiner

*Primary Examiner*—George Manuel
*Assistant Examiner*—Shubatra Narayanaswamy

(57) ABSTRACT

Apparatus and methods are provided for delivering a lead over a rail into a target body lumen, cavity, or other vessel, e.g., a coronary vein or a right ventricle within a patient's heart. For example, a distal end of an elongate guidewire or other rail may be introduced into the coronary venous system via the coronary sinus, advanced through the coronary venous system to a location beyond a target vessel, and secured at the location beyond the target vessel. A catheter or other elongate tubular member is advanced over the rail and manipulated to position an outlet of the tubular member adjacent to or otherwise aligned relative to the target vessel. A distal end of a lead is delivered through the tubular member and out the outlet into the target vessel. The catheter and rail are then removed, leaving the lead within the target vessel.

12 Claims, 4 Drawing Sheets

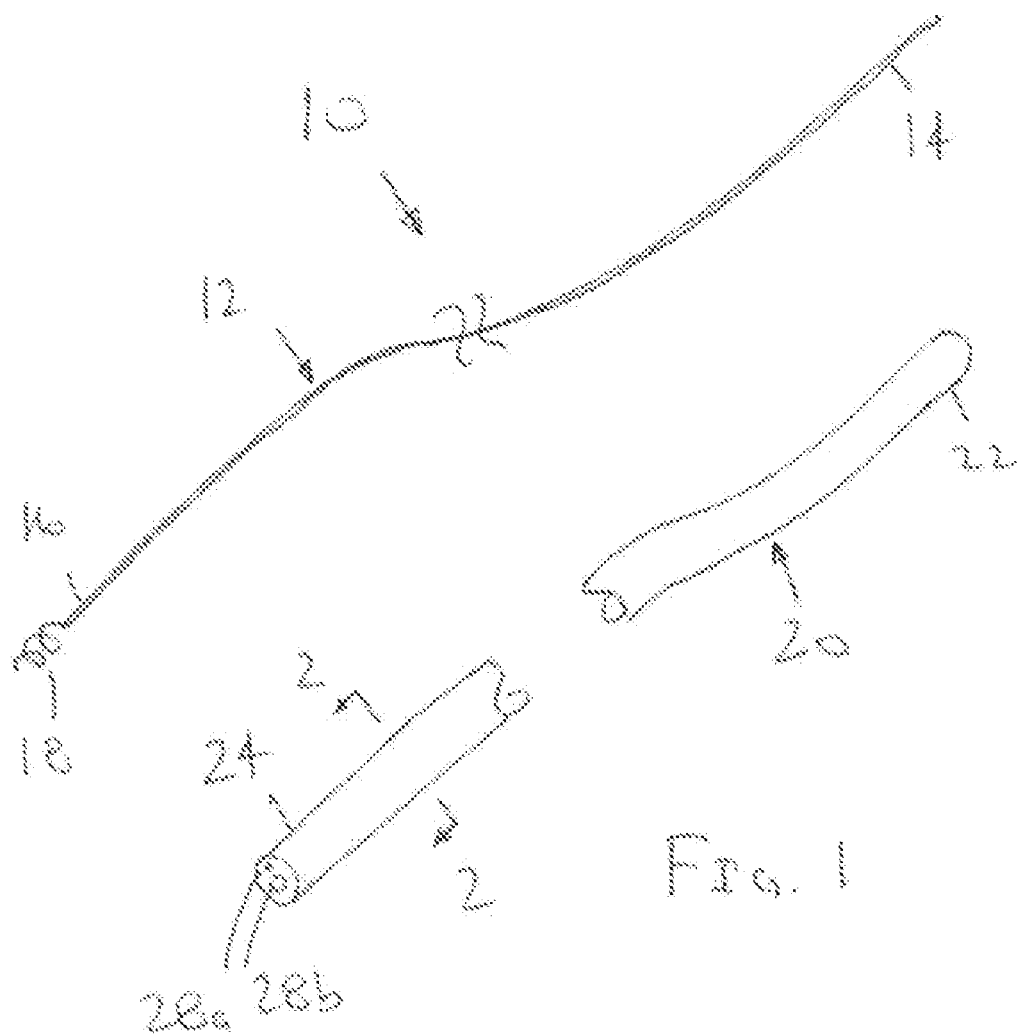
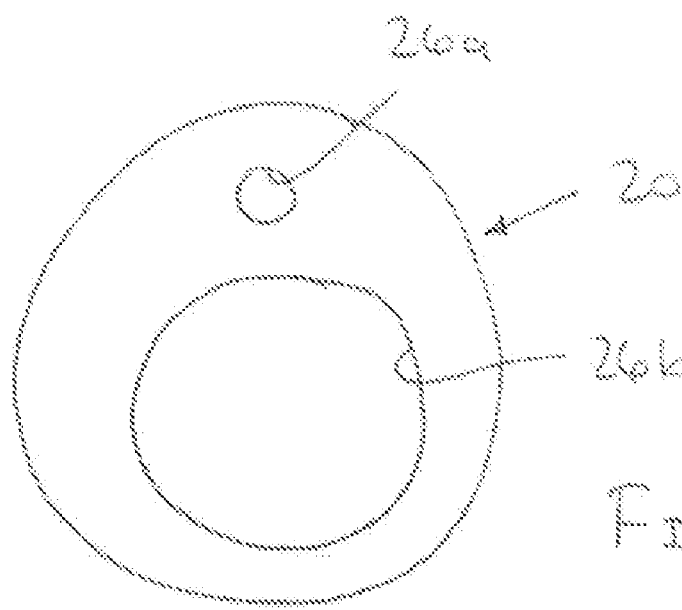

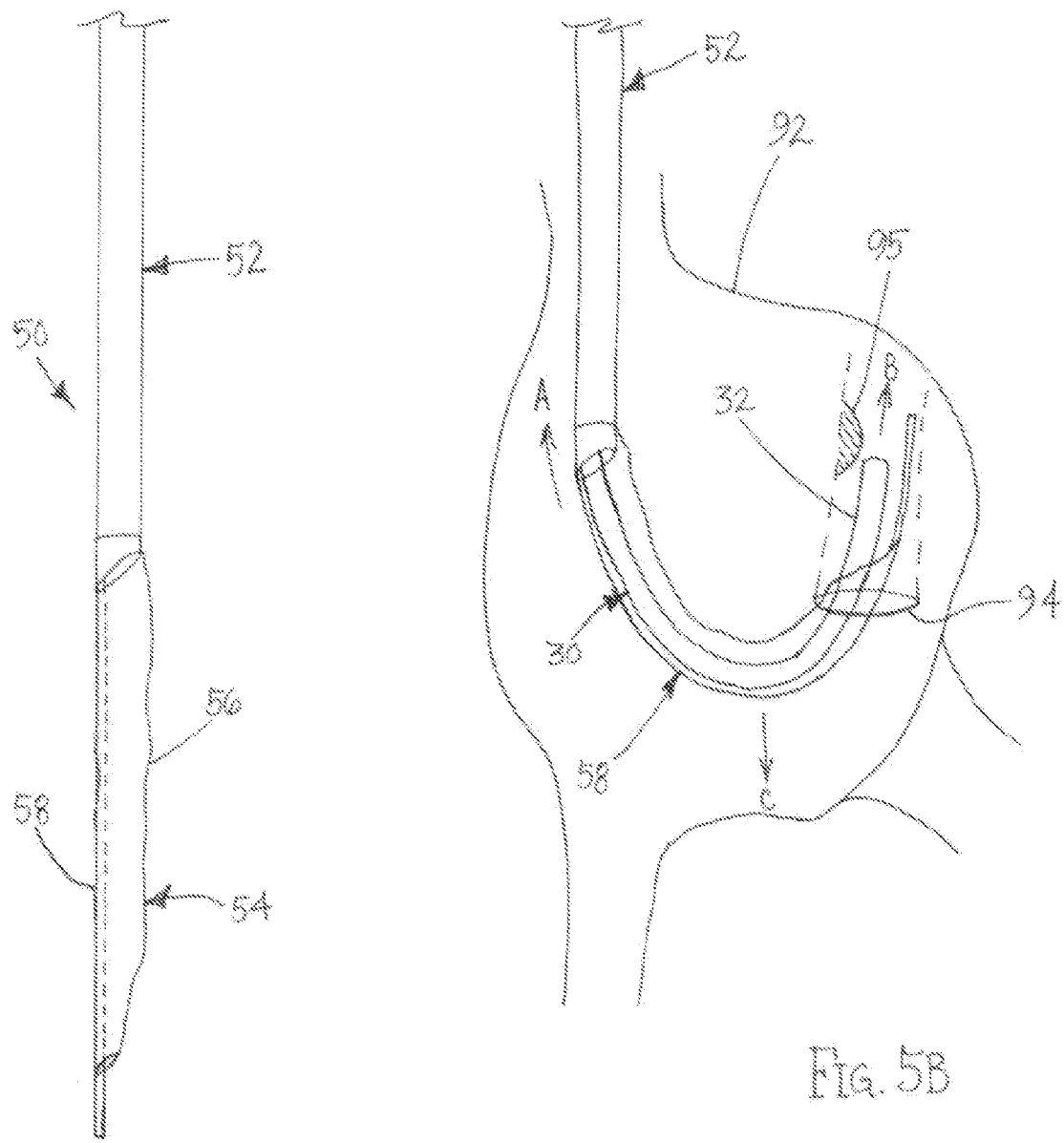

APPARATUS AND METHODS FOR DELIVERING TRANSVENOUS LEADS

This application claims benefit of Provisional Application Ser. No. 60/708,750 filed Aug. 16, 2005, the entire disclosure of which is expressly incorporated by reference herein.

FIELD OF THE INVENTION

The present invention relates generally to apparatus and methods for delivering leads, and, more particularly, to apparatus and methods for delivering leads or other instruments using a delivery device movable over a guidewire or other rail.

BACKGROUND

It is known to place pacing leads in the area of the left ventricle via the coronary veins, e.g., for bi-ventricular pacing or resynchronization therapy. During such procedures, an electrical conductor (i.e., pacing lead) must be coupled to the left ventricle. In order to accomplish this in a minimally invasive fashion, the most common approach is by way of the coronary sinus and coronary venous system.

Such an approach can be difficult for a number of reasons. These include the inherent variability of venous anatomy, the multiplicity of turns that a device must take when tracking into the coronary sinus and/or its tributaries by way of subclavian or femoral vein approach, and the anatomical distortion that occurs secondary to diseases of the heart, as for example, heart failure or atrial fibrillation.

Furthermore, the design objectives of a lead system optimized for delivery often conflict with the design objectives of a system optimized to remain in stable position for long term pacing. For example, during delivery, a device is optimally lubricious and slides easily through the vasculature; however, once in place, the optimal device does not slide easily out of place, but remains in a stable position. As another example, during delivery, an optimal device has stiffness characteristics optimized to track around initial bends into the open chamber of the right atrium, into the lumen of the coronary sinus, and turn yet again into its tributaries. The optimal device during delivery should be pushable and hence have some degree of stiffness, whereas once in position the optimal device is generally flexible with high fatigue resistance. Furthermore, where the lead system specifically also includes a delivery component (e.g., sheath, guidewire, stylet, and the like) that is not left in the body, this component must be removed. Therefore, during introduction it is generally advantageous for his component to be stiffer and pushable, whereas during removal these properties may tend to dislodge the lead from it stable position.

Another problem associated with transvenous lead delivery is maintaining stable access into the coronary sinus and the coronary veins. Initial access of the coronary sinus may be difficult secondary to the presence of venous valve or tortuous or distorted anatomy. Once the coronary sinus has been accessed with a sheath or guidewire or other device, maintaining access is important and may be difficult during multiple exchanges of devices, for example a venography balloon catheter or pacing lead, or when attempting to move a pacing lead from one position to anther position.

Accordingly, apparatus and methods for delivering leads would be useful.

SUMMARY OF THE INVENTION

The present invention is directed generally to apparatus and methods for delivering leads and/or other instruments during a medical procedure. More particularly, the present invention is directed to apparatus and methods for delivering leads into one or more vessels, e.g., within a patient's coronary venous system.

Generally, transvenous leads or other instruments may be delivered using a rail, such as a guidewire, which may be secured at a location within the vasculature not entirely on the path to the final desired lead position. The rail may become a stable component of a delivery system that may remain in place during one or more stages of a procedure, for example, during a venogram, lead introduction, lead repositioning, and the like.

The coronary venous system may provide a useful anatomical pathway with respect to lead delivery using such an approach. Generally, the anterior vein is not considered an ideal site for pacing given its anatomical location over the septum of the heart, while the posterior and posterolateral veins are considered to be superior locations for pacing. Therefore, a rail may be placed in the anterior vein to maintain stable access which the remaining delivery system may be designed to interface with this rail.

Using the rail, a device may be delivered that is adapted to track along the rail and also provide a path for delivering a lead or other instrument, although the path diverges from that of the rail at an appropriate point, e.g., at a location the point a posterior or posterolateral branch is encountered.

In accordance with one embodiment, a system is provided for delivering a pacing lead into a body lumen that includes an elongate rail including a proximal end, a distal end sized for introduction into a body lumen, and an anchor on the distal end for securing the distal end to tissue within a body lumen; and an elongate tubular member including a proximal end, a distal end sized for introduction into a body lumen, and first and second lumens extending between the proximal and distal ends. The first lumen may be provided for receiving the rail therethrough such that the tubular member is advanceable over the rail, while the second lumen is sized for receiving a pacing lead therethrough. In addition, the system may include a pacing or other transvenous lead receivable within the second lumen.

In accordance with another embodiment, a method is provided for delivering an instrument within a branch body lumen or body cavity communicating with a main body lumen or body cavity. A distal end of an elongate rail may be introduced into the main body lumen, and advanced to a location beyond the branch body lumen. The distal end may be secured at the location beyond the branch body lumen, e.g., thereby providing a rail extending along the main body lumen. An elongate tubular member may be advanced over the rail, the elongate tubular member including an outlet communicating with an instrument lumen, and the outlet may be aligned with the branch body lumen. An instrument, e.g., a transvenous lead, may be introduced through the instrument lumen and out the outlet into the branch body lumen.

In accordance with still another embodiment, a method for delivering a lead into a target coronary vein within a patient's heart. A distal end of an elongate rail may be introduced into the coronary venous system via the coronary sinus, advanced through the coronary venous system to a location beyond a target coronary vein, and secured at the location beyond the target coronary vein. An elongate tubular member may be advanced over the rail and manipulated to position an outlet of the tubular member adjacent to or otherwise aligned relative to the target coronary vein. A distal end of a lead is delivered through the tubular member and out the outlet into the target coronary vein.

In accordance with yet another embodiment, a method is provided for delivering an instrument within a body cavity communicating with a main body lumen or body cavity. A distal end of an elongate rail may be introduced into the body cavity, e.g., the right ventricle, and advanced to a location beyond the body cavity, e.g., into the pulmonary artery or other body lumen of cavity. The distal end may be secured at the location beyond the body cavity, e.g., thereby providing a rail extending through the body cavity. An elongate tubular member may be advanced over the rail, the elongate tubular member including an outlet communicating with an instrument lumen, and the outlet may be aligned with the branch body lumen. An instrument, e.g., a transvenous lead, may be introduced through the instrument lumen and out the outlet into the body cavity. The instrument may be secured within the body cavity, e.g., secured to tissue using a helical screw or other fixation device, or simply inserted with sufficient force to frictionally engage surrounding tissue.

Other aspects and features of the present invention will become apparent from consideration of the following description taken in conjunction with the accompanying drawings.

BRIEF DESCRIPTION OF THE DRAWINGS

FIG. 1 is a perspective view of a system for delivering a pacing lead or other instrument, including a guidewire and a delivery catheter.

FIG. 2 is a cross-section of the delivery catheter of FIG. 1, taken along line 2-2.

FIG. 5A is a side view of an embodiment of a delivery apparatus including a flexible sheath supported by a backbone for delivering a lead.

FIG. 5B is a detail of a patient's heart, showing a lead being delivered using the apparatus of FIG. 5A.

DETAILED DESCRIPTION

Figure 3:
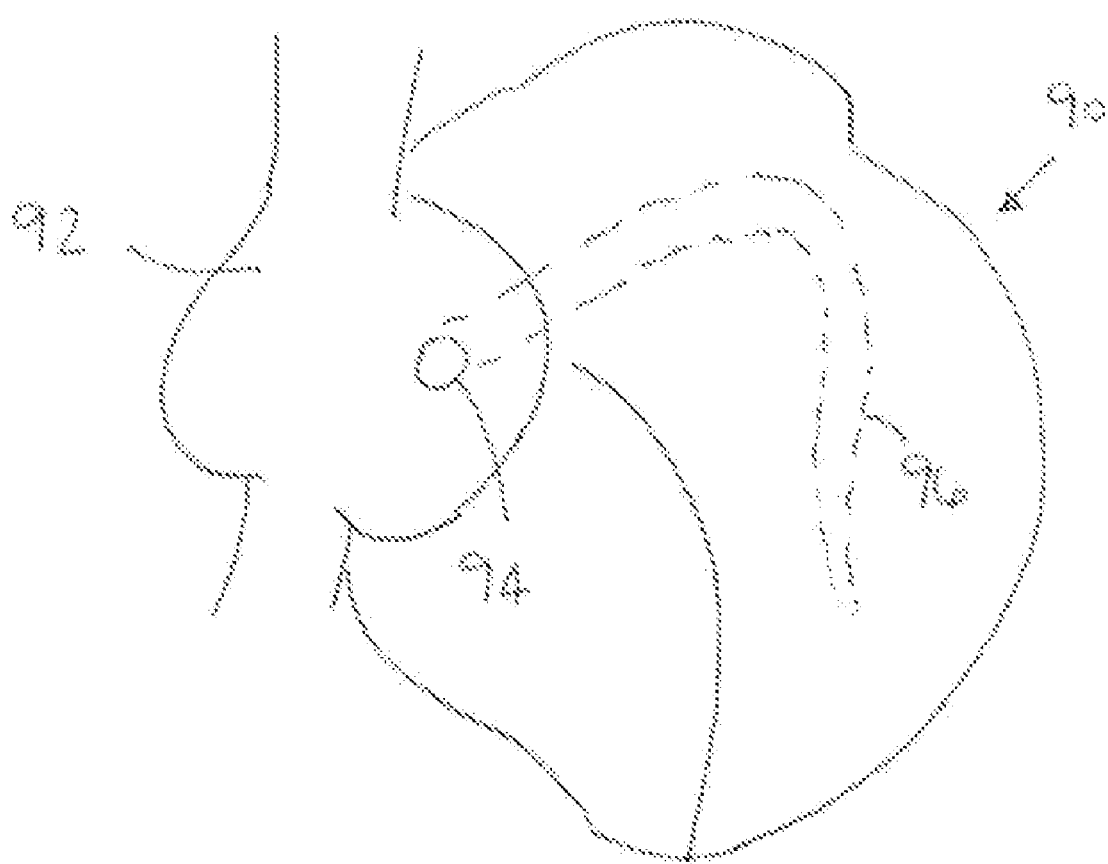
FIG. 3 is a schematic view of a heart showing the right atrium, coronary sinus, and anterior coronary vein.

Turning to the drawings, FIG. 1 shows an exemplary embodiment of a system 10, including a guidewire or other elongate rail 12 and a catheter or other tubular member 20. The system 10 may be used for delivering a lead, e.g., a pacing or other transvenous lead (not shown), or other instrument to a location within a body lumen, as described further below.

The guidewire 12 generally includes a proximal end 14, a distal end 16, and an anchor or other fixation device 18 on the distal end 16. The guidewire 12 may be formed using known materials and methods, e.g., metal, such as stainless steel or Nitinol, plastics, or composite materials. For example, the guidewire 12 may be formed from a single strand of solid or hollow wire, multiple strands, and the like. The guidewire 12 has sufficient length to extend from a location outside a patient's body, e.g., from a percutaneous entry site into the subclavian or femoral vein, to a target location where the distal end 16 is to be secured.

The anchor 18 may include any device capable of securing the distal end 16 to tissue or otherwise within a body lumen or body cavity, e.g., a helical coil, a barbed tip, hook, a balloon or other expandable device, and the like. The anchor 18 may be attached to the distal end 16 or integrally formed thereon. Alternatively, other elongate rails may be provided instead of guidewire 12, e.g., an elongate catheter, sheath, or other member (not shown), which is sized to be received in the catheter 20 and includes an anchor on its distal end.

With continued reference to FIG. 1 and additional reference to FIG. 2, the catheter 20 is an elongate tubular body including a proximal end 22, a distal end 24 sized for introduction into a body lumen, and one or more lumens 26 extending therebetween. As shown in FIG. 2, the catheter 20 includes a first lumen 26a for receiving the guidewire or other rail therethrough, and a second lumen 26b for receiving a lead or other instrument therethrough. As shown, the first lumen 26a may be smaller than the second lumen 26b. For example, the first lumen 26a may have a diameter between about 0.1 and one millimeter, while the second lumen 26b may have a diameter between about 0.3 and one hundred millimeters (0.3-100 mm), or between about 0.3 and twenty millimeters (0.3-20 mm).

One or more outlets 28 may be provided at the distal end 24 that communicate with respective lumens 26. As shown in FIG. 1, a first outlet 28a is provided that communicates with the first lumen 26a, and a second outlet 28b is provided that communicates with the second lumen 26b. As shown, the outlets 28 may be disposed adjacent one another disposed axially, i.e., oriented along a longitudinal axis of the catheter 20. Alternatively, the outlets 28 may be offset axially from one another and/or oriented laterally. For example, if it is desired to deliver an instrument laterally from the catheter 20, the second outlet may be disposed proximal to the first outlet, e.g., in a side wall of the catheter 20, rather on the distal tip. In such an alternative, the second lumen may include a ramp or other transition (not shown) for directing an instrument advanced through the second lumen out the lateral outlet.

As a further alternative to the catheter 20 shown in FIGS. 1 and 2, other delivery devices may be provided that may be directed over the guidewire 12 or other rail. For example, patent application Ser. No. 10/423,321, filed Apr. 24, 2003, patent application Ser. No. 10/958,034, filed Oct. 4, 2004, and patent application Ser. No. 11/347,361, filed Feb. 3, 2006 disclose expandable sheath apparatus that may be used to deliver a lead or other instrument. The entire disclosures of these references are expressly incorporated by reference herein. In such apparatus, one lumen may provide a guidewire lumen, e.g., a lumen within a stiffening member or backbone (not shown), and an expandable lumen defined at least partially by an expandable sheath may provide an instrument lumen (also not shown).

Turning to FIGS. 3 and 4A-4D, apparatus and systems as described herein may be used for delivering an instrument, e.g., a pacing or other transvenous lead 30, into a target vessel or other body lumen within a patient's body. For example, FIG. 3 shows a heart 90 that includes a right atrium 92, a coronary sinus 94 extending from the right atrium 92, and one or more coronary veins communicating with the coronary sinus 94 to define the coronary venous system of the heart. In FIG. 3, only the anterior vein 96 is shown in phantom for simplicity.

Figure 4A:
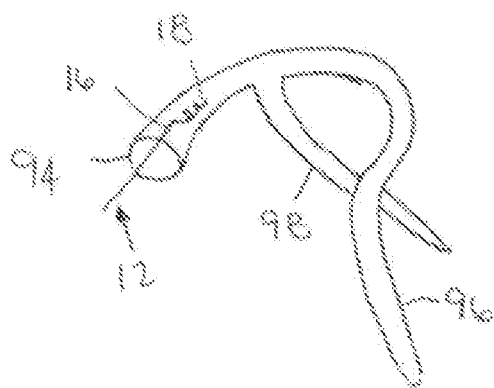
FIGS. 4A-4D are details of a portion of the heart of FIG. 3, showing a method for delivering a lead into a target coronary vein using a delivery a device over a rail.

Turning to FIG. 4A, the guidewire 12 (or other rail) may be introduced into a patient's vasculature, e.g., from a percutaneous entry site into a subclavian or femoral vein, and advanced through the superior vena cava (not shown), the right atrium (also not shown), and into the coronary sinus 94 using known methods. Exemplary apparatus and methods for delivering a guidewire or other rail into the coronary sinus are disclosed in U.S. Pat. No. 6,979,290, issued Dec. 27, 2005, and patent application Ser. No. 11/057,074, filed Feb. 11, 2005, patent application Ser. No. 11/062,074, filed Feb. 17, 2005, and patent application Ser. No. 11/379,562, filed Apr.

20, 2006. The entire disclosures of these references are expressly incorporated by reference herein.

Figure 4B:
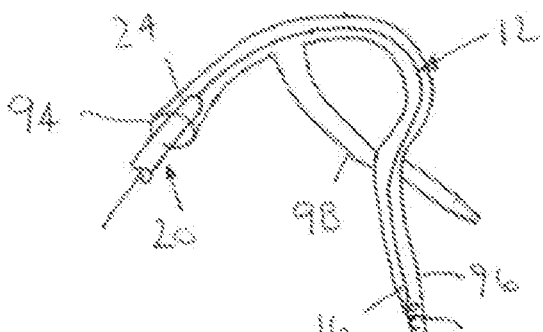

As shown in FIG. 4A, coronary vein 98 may be selected as a target location for placing a lead or other instrument. The guidewire 12 is advanced such that the distal end 16 is directed past the target coronary vein 98 and further into the coronary venous system, e.g., into the anterior vein 96. Turning to FIG. 4B, the distal end 16 of the guidewire 12 may be secured within the anterior vein 96 (or other desired location beyond the target coronary vein 98) using the anchor 18. For example, the guidewire 12 may be twisted or otherwise rotated about its longitudinal axis to thread a helical anchor into the wall and/or other tissue adjacent the anterior vein 96. Alternatively, if an expandable anchor is provided, the anchor may simply be expanded to frictionally engage the wall of the anterior vein 96, thereby preventing substantial movement of the distal end 16. In additional alternatives, the guidewire or other rail may be secured to tissue or other structures at other locations, e.g., within to the wall of a chamber of the heart, to tissue within the pericardial space or thoracic cavity, or other body cavity.

As explained elsewhere herein, the anterior vein 96 is generally not considered a good candidate for lead placement because of its location above the septum of the heart. Thus, positioning and securing the distal end 16 of the guidewire 12 within the anterior vein 96 may not interfere with accessing target veins between the coronary sinus 94 and the anterior vein 96, yet provide an anchor point. Thus, the guidewire 12 may then provide a substantially stable rail over which other devices, such as catheter 20, may be advanced.

Figure 4C:
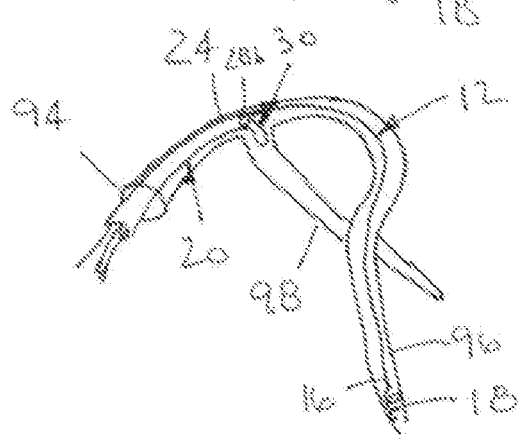

Turning to FIGS. 4B and 4C, catheter 20 (or one or more other devices) may then be advanced over the guidewire 12 into the coronary venous system via the coronary sinus 94. For example, with additional reference to FIG. 1, a proximal end 14 of the guidewire 12 may be backloaded into the outlet 28a of the catheter 20, and advanced through the first lumen 26a. The distal end 24 of the catheter 20 may then be introduced into the patient's body at the entry site, and advanced over the guidewire 12 into the heart and coronary sinus 94, as shown in FIG. 4B.

As shown in FIG. 4C, the catheter 20 may be advanced until the distal end 24, in particular, the outlet 28b, is disposed adjacent to the target coronary vein 98. The guidewire allows the catheter 20 to be introduced over the rail and moved forward and/or back along the rail without fear of losing access to the coronary sinus because the rail is placed securely in the anterior vein 96. Optionally, external imaging, e.g., fluoroscopy, may be used to monitor and/or facilitate manipulation of the catheter 20.

Figure 4D:
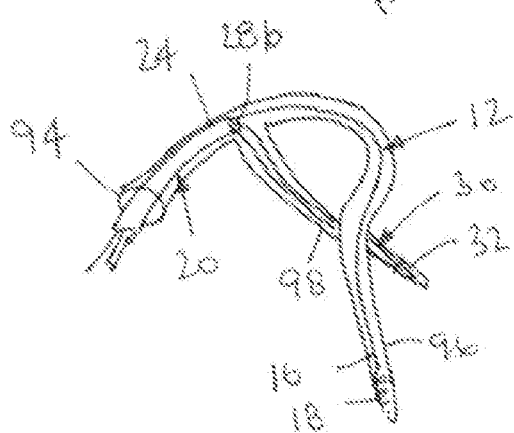

In one embodiment, the target coronary vein 98 may include one of the posterior or posterolateral veins, which are often a desired site for lead placement. The outlet 28b of the catheter 20 may be positioned adjacent to the entry of the target coronary vein 98, and a lead 30 may be advanced through the catheter 20 and out the outlet 28b into the target coronary vein 98. As shown in FIG. 4D, the lead 30 may be advanced into the target coronary vein 98, e.g., until one or more electrodes 32 are disposed at a desired location, e.g., deep within the target coronary vein 98.

The lead 30 may be loaded directly into the proximal end 22 (not shown, see FIG. 1) of the catheter 20 and advanced through the second lumen 26b (also not shown, see FIG. 2), and out the outlet 28b. Alternatively, the lead 30 may be preloaded within the catheter 20 before the catheter 20 is introduced into the patient's body. In a further alternative, the lead 30 may be directed and/or advanced into the target coronary vein 98 using one or more additional devices. For example, before introducing the lead 30, an additional guidewire (not shown) may be directed through the second lumen 28b of the catheter 20 and advanced out the outlet 28b and into the target coronary vein 98. The lead 30 may then be advanced over the additional guidewire, which may facilitate advancing the lead 30 deep within the target coronary vein 98. Alternatively, an expandable sheath apparatus, such as those disclosed in the applications incorporated by reference above (not shown), may be introduced through the catheter 20 and into the target coronary vein 98, and the lead 30 may be directed through the expandable sheath.

If an initial target coronary vein is determined not to be therapeutically optimal, e.g., because of its location relative to the left ventricle or other anatomy to be stimulated, the lead 30 may be retracted from its position within the target coronary vein 98 without fear of losing access because of the rail that is in a stable position and not along the main path of lead delivery. For example, the lead 30 may be withdrawn into or removed entirely from the catheter 20, and the catheter 20 may be directed to another vessel extending from the path provided by the secured guidewire 12. Once a second target vessel is identified and accessed using the catheter 20, the lead 30 may be redeployed and advanced into the second target vessel.

Once the lead 30 is placed within a desired target vessel, the catheter 20 may be withdrawn from the venous system through the coronary sinus 94 and removed from the patient's body, leaving the lead within the target vessel. The guidewire 12 may also be removed, e.g., by unscrewing or otherwise disengaging the anchor 18, and withdrawing the guidewire 12 from the coronary venous system via the coronary sinus 94. The guidewire 121 may be removed before or after the catheter 20.

Additionally, other devices or agents may be delivered using the systems and method during the procedures described above or during other procedures. For example, contrast may be infused from the catheter 20, e.g., as the catheter 20 is moved along the guidewire 12 in order to visualize venous tributaries fluoroscopically. Thus, the catheter 20 may be manipulated along the path provided by the secured guidewire 12 to identify a target vessel for lead placement or other diagnosis and/or treatment.

In addition, the rail apparatus and methods described here may be used to identify initially a target vessel or other implantation site for a lead or other device. For example, an imaging or visualization device, such as a fiberoptic imaging catheter may be advanced over the guidewire 12 to visualize directly the path and identify a site for implantation or other treatment. Exemplary imaging catheters are disclosed in the references incorporated by reference above. Such an imaging catheter may be provided within a balloon or other clear surface through which imaging may occur, or the balloon may be eliminated. In addition, a rail, such as the guidewire 12, may be used to deliver a lead over the rail, e.g., using the apparatus and methods disclosed in application Ser. No. 11/465,123 filed Aug. 16, 2006, entitled, "Apparatus and Methods for Placing Leads Using Direct Visualization".

In addition to the concepts disclosed above, additional apparatus and methods may be provided for delivering leads into the coronary sinus or other body lumen. In the process of delivering leads it is advantageous to maximize pushing forces that are translated from pushing at the proximal end of the lead to the lead tip. One method of translating pushing forces, e.g., for "floppy" or other flexible leads, is to use the elastic recoil of a lubricious delivery sheath, such as those disclosed in the references incorporated by reference above. FIG. 5A shows an exemplary delivery sheath 50, including a substantially rigid or semi-rigid proximal segment 52 and a substantially flexible distal segment 54 that includes a tubular thin membrane 56 attached to a substantially rigid or semi-rigid backbone 58.

FIG. 5B shows a lead 30 being introduced through the apparatus 50. The apparatus 50 has been introduced into a patient's heart such that the distal segment 54 extends through the right atrium 92 into the coronary sinus 94, similar to previous embodiments described herein. As shown, a stenosis 95 exists within the coronary sinus 94, which may create resistance against easy advancement of a distal tip 32 of the lead 30. As the lead 30 is advanced by pushing at its proximal end (not shown), the tip 32 encounters resistance and the thin membrane of the sheath 30 is stretched in direction C. If the proximal end of the lead 30 is held in place and not allowed to relax, the recoil of the membrane of the sheath 30 pushes against the lead 30 in a direction opposing direction C. Because the lead 30 is restrained from moving backward in direction A, the recoil force is translated into direction B, e.g. toward the distal tip 32 of the lead 30, forcing the lead through and beyond the stenosis 95. The efficiency of this translation of force may be affected by the friction and elasticity properties of the membrane material.

To facilitate delivering leads, e.g., into a target coronary vein or other vessel, it may be desirable to include a lubricious interface between the lead and surrounding tissue or devices. For example, a temporary lubricious interface may be provided between the lead being delivered and the vasculature to reduce friction and/or otherwise facilitate delivery. A temporary lubricious interface may be useful, because, once a lead is placed and secured, such a lubricious interface may be undesirable, since it may cause the lead to slip or dislodge subsequent to placement. Thus, it may be desirable to remove or alter the lubricious interface following delivery in order to minimize the likelihood of acute or chronic dislodgement of the lead from a stable position.

Such a temporary lubricious interface may be accomplished by a number of ways. For example, the lead may be provided with a lubricious coating, for example a hydrophilic coating that is adapted to wear off over a predictable duration. Most hydrophilic coatings are intended to extend the life of the coating, rather than shorten the life. In the case of lead delivery, however, a limited working life of such a coating would be advantageous. In one case, the coating may be applied such that it wears off relatively quickly, largely by mechanical wear, e.g., under normal use conditions encountered during delivery. In another embodiment, a de-activating agent or energy may be introduced to change the properties of the coating, or even to make it have subsequently increased friction beyond that between the lead alone and the vasculature. A further embodiment might entail using an apparatus to speed mechanical wear of the coating.

Another option may entail introducing a lubricant into the vasculature or path of introduction of the lead that temporarily makes the path more lubricious. The lubricant may subsequently dissipate naturally, e.g., due to normal fluid flow, such that introduction of the lead is facilitated but once in place the final position is stable.

Still another option may entail disposing a lubricious interface along the lead during introduction and removing the interface following final placement of the lead. For example, a thin film, such as PTFE or other thin film with lubricious coating, or other lubricious material may be initially disposed along the lead. During introduction, the lubricious interface may facilitate delivering the lead easily through the vasculature, sheath or other component of the delivery pathway. Once the lead is in its final position, the thin film may then be removed, for example, by sliding back or by other methods, thereby exposing the surface of the lead to the surrounding vessel wall. Generally, the exposed lead surface may be less lubricious than the lubricious interface and therefore may facilitate stability of the lead in its final position.

Alternatively, a lubricious interface may be introduced into the vasculature or other body lumens before delivering a lead, such as the expandable sheath apparatus disclosed in the references incorporated by reference above.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

We claim:

1. A method for delivering an instrument to a target location within a patient's vasculature, the method comprising:
   introducing a distal end of an elongate rail into the vasculature;
   advancing the distal end of the rail to a location beyond the target location;
   securing the distal end of the rail at the location beyond target location by threading a helical anchor of the rail into adjacent tissue;
   introducing an elongate tubular member over the secured rail by backloading a proximal end of the secured rail into a first lumen of the elongate tubular member, via a first outlet of the first lumen, the first lumen extending between a proximal end and a distal end of the tubular member, and the first outlet being at the distal end of the tubular member;
   advancing the elongate tubular member over the secured rail until a second outlet of a second lumen of the elongate tubular member is adjacent to the target location, the second lumen extending between the proximal end and the distal end of the tubular member, and the second outlet being in proximity to the distal end of the tubular member; and
   delivering the instrument through the second lumen and out the second outlet to the target location.

2. The method of claim 1, wherein the instrument comprises a pacing lead.

3. The method of claim 1, further comprising securing the instrument at the target location.

4. The method of claim 1, wherein the target location and the location beyond the target location are located in a coronary venous system of the patient's vasculature.

5. The method of claim 4, wherein the target location is a first coronary vein and the location beyond the target location is a second coronary vein.

6. The method of claim 5, wherein the first coronary vein is one of: a posterior vein and a posterolateral vein, and the second coronary vein is an anterior vein.

7. The method of claim 5, further comprising:
   directing a guidewire through the second lumen of the elongate tubular member and out the second outlet of the second lumen into the first coronary vein; and
   wherein delivering the instrument comprises advancing the instrument over the directed guidewire deep within the first coronary vein.

8. The method of claim 5, wherein the instrument comprises a pacing lead; and further comprising advancing the delivered pacing lead into the first coronary vein until an electrode of the lead is disposed deep within the first coronary vein.

9. The method of claim 5, further comprising:
retracting the instrument from the first coronary vein and into the second lumen of the elongate tubular member;
directing the elongate tubular member over the secured rail until the second outlet of the second lumen is adjacent another target location; and
advancing the instrument back out the second outlet to the other target location;
wherein the other target location comprises a third coronary vein; and
the location at which the distal end of the rail is secured is beyond the other target location.

10. The method of claim 1, further comprising removing the elongate tubular member and the rail from the patient's vasculature while the instrument remains at the target location.

11. The method of claim 10, wherein removing the rail comprises unscrewing the anchor from the tissue.

12. The method of claim 1, further comprising preloading the instrument within the elongate tubular member prior to introducing the elongate tubular member over the secured rail.

* * * * *